United States Patent [19]

DeLuca et al.

[11] Patent Number: 5,366,731
[45] Date of Patent: Nov. 22, 1994

[54] COSMETIC COMPOSITIONS CONTAINING SECOSTEROL COMPOUNDS

[75] Inventors: Hector F. DeLuca, Deerfield; Connie M. Smith, Madison, both of Wis.

[73] Assignee: Wisconsin Alumni Research Foundation, Madison, Wis.

[21] Appl. No.: 13,260

[22] Filed: Feb. 3, 1993

Related U.S. Application Data

[63] Continuation of Ser. No. 572,857, Aug. 24, 1990, abandoned.

[51] Int. Cl.$^5$ .............................................. A61K 31/59
[52] U.S. Cl. .................................... 424/401; 514/167
[58] Field of Search ........................ 424/401; 514/167

[56] References Cited

U.S. PATENT DOCUMENTS

| | | | |
|---|---|---|---|
| Re. 33,107 | 11/1989 | Dikstein et al. | 514/46 |
| 4,610,978 | 9/1986 | Dickstein et al. | 514/46 |
| 4,728,643 | 3/1988 | Holick et al. | 514/167 |
| 4,800,198 | 1/1989 | DeLuca et al. | 514/167 |

FOREIGN PATENT DOCUMENTS 62-169711 7/1987 Japan.

*Primary Examiner*—Thurman K. Page
*Assistant Examiner*—Neil Levy
*Attorney, Agent, or Firm*—Andrus, Sceales, Starke & Sawall

[57] ABSTRACT

Compositions containing secosterol compounds in a suitable carrier and methods employing such compositions are disclosed for cosmetic uses in the treatment of various skin conditions such as lack of adequate skin firmness, wrinkles, dermal hydration and sebum secretion. Various formulations of the compositions including creams, lotions and ointments are disclosed for use topically, orally or parenterally in accordance with this invention

5 Claims, 3 Drawing Sheets

FIG. 1

COSMETIC COMPOSITIONS CONTAINING SECOSTEROL COMPOUNDS

This application is a continuation of application Ser. No. 07/572,857, filed Aug. 24, 1990, now abandoned.

BACKGROUND OF THE INVENTION

The present invention relates to cosmetic compositions, and more particularly to such compositions containing secosterol compounds.

Skin problems range between severe skin disorders such as dermatitis, eczema, psoriasis, solar keratosis and the like, and less severe skin conditions such as wrinkles, lack of dermal hydration i.e. dry skin, lack of adequate skin firmness i.e. skin slackness, insufficient sebum secretion and the like. The former skin disorders have typically been treated with compositions termed "dermatological" whereas the latter skin conditions have typically been treated with compositions termed "cosmetic" since the primary functions of such compositions are to preserve, condition or protect the skin.

In the past, treatment of various skin disorders and skin conditions has been largely based on non-specific-drugs. For example, dermatitis has been commonly treated with corticosteroids. Such compounds may provide symptomatic relief for some patients. However, steroids are known to produce numerous local and systemic side effects, and their long term use is not recommended.

Holick et al U.S. Pat. No. 4,728,643 discloses a method of treating psoriasis by administering to a patient a Vitamin D compound capable of differentiating cultured tumor cells. Examples of such compounds are vitamins $D_2$ or $D_3$ or derivatives of vitamins $D_2$ or $D_3$.

Dikstein et al U.S. Pat. No. 4,610,978 and U.S. Reissue Pat. No. 33,107 disclose cosmetic and dermatological compositions containing 1 alpha-hydroxycholecalciferol or 1 alpha, 25-dihydroxycholecalciferol. These compositions are disclosed for use in the topical treatment of skin disorders and skin conditions such as dermatitis, psoriasis, eczema, solar keratosis, wrinkles, dry skin and skin slackness.

Japanese published patent application No. 62/169711 entitled "A Skin Cosmetic Material" discloses a skin cosmetic composition containing vitamin $D_3$ and/or vitamin $D_3$ derivatives. The vitamin $D_3$ derivatives disclosed include 25-hydroxycholecalciferol, 1 alpha-hydroxycholecalciferol, 5,6-trans-25-hydroxycholecalciferol, 1 alpha-25-dihydroxycholecalciferol and dihydrotachysterol.

Finally, DeLuca et al U.S. Pat. No. 4,800,198 discloses the structure of the secosterol compounds of interest in the present compositions. However, the patent is directed toward a method for inducing the differentiation of malignant cells utilizing secosterol compounds, and in particular to the treatment of leukemoid diseases with such compounds. The patent does not teach or suggest any cosmetic uses for the secosterol compounds disclosed therein.

SUMMARY OF THE INVENTION

Cosmetic compositions containing one or more secosterol compounds and a suitable carrier useful in the treatment of various skin conditions are described. The treatment may be topical, oral or parenteral. Methods of employing the compositions are also disclosed. The compounds are present in the composition in an amount from about 0.001 μg/gm to about 10.0 μg/gm of the composition, and may be administered orally or parenterally in dosages of from about 0.1 μg/day to about 25 μg/day.

In one aspect of the invention, cosmetic compositions containing one or more secosterol compounds for the treatment of skin conditions such as wrinkles, lack of dermal hydration i.e. dry skin, lack of adequate skin firmness i.e. slack skin, and insufficient sebum secretion are provided. Methods employing the cosmetic compositions are also provided.

Various formulations for the cosmetic compositions are also provided. Such formulations may include creams, lotions, ointments, and the like. The compositions and/or formulations may also include additional active ingredients if desired.

The compounds disclosed herein unexpectedly provide highly effective treatments for the above skin conditions without producing unwanted systemic or local side effects.

DETAILED DESCRIPTION OF THE INVENTION

Figure 1:
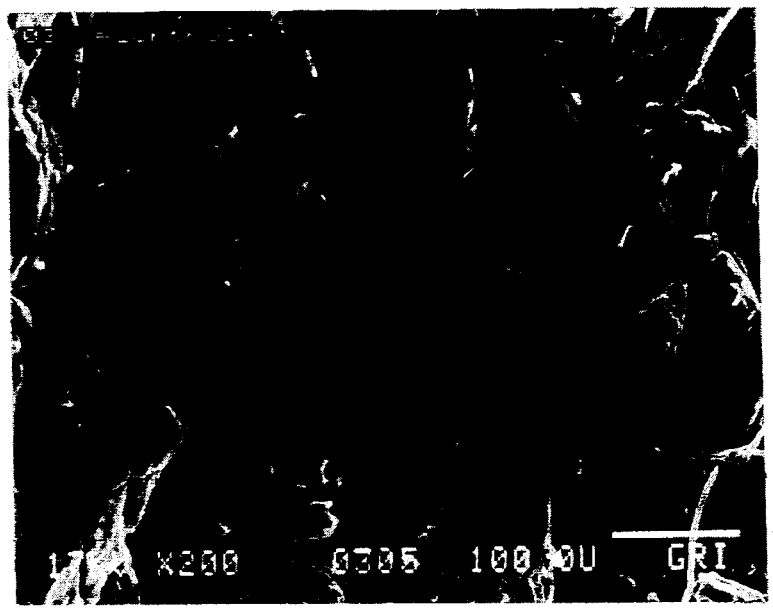
FIG. 1 is a photomicrograph at ×200 magnification of a skin replica of a control mouse treated topically with a propylene glycol control vehicle.

It has now been found that effective treatment of various skin conditions can be achieved with compositions which include an effective amount of a secosterol compound.

Purely structually, this class of secosterols has similarity with some of the known vitamin D compounds. Unlike the known vitamin D compounds, however, the secosterols used in the present invention do not express the classic vitamin D activities in vivo, i.e. stimulation of intestinal calcium transport, or the mobilization of bone calcium, and hence they cannot be classified as vitamin D derivatives from the functional point of view. In light of the prior art, it was all the more surprising and unexpected then, to find that these secosterols are remarkably effective in the treatment of skin conditions. This finding provides an effective method for the treatment of skin conditions, since the above described secosterols can be administered to subjects in doses sufficient to treat the skin condition, without producing simultaneously unphysiologically high and deleterious blood calcium levels.

The group of secosterols exhibiting this unique and heretofore unrecognized activity pattern is characterized by the general structure I shown below:

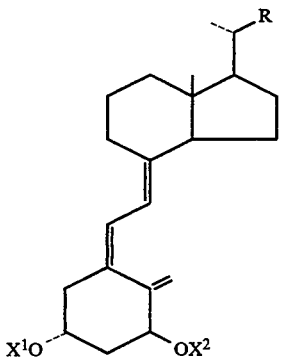

where R is hydrogen, methyl, ethyl or propyl and where each of $X^1$ and $X^2$ represent, independently, hydrogen, an acyl group, or a hydroxy-protecting group.

As used in this description and the claims, the term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl" and "fluoroalkyl" refer to such an alkyl radical substituted by one or more hydroxy or fluoro groups respectively. An "acyl" group is an alkanoyl group of 1 to 6 carbons in all its isomeric forms, or an aroyl group, such as benzoyl, or halo-, nitro- or alkyl-substituted benzoyl groups, or a dicarboxylic acyl group such as oxalyl, malonyl, succinoyl, glutaroyl, or adipoyl.

Secosterol of structure I where R is hydrogen can be prepared according to the method of Lam et al as published in Steroids 26., 422 (2975), the description of which is specifically incorporated herein by reference. The secosterols of structure I, where R is methyl, ethyl or propyl, can be prepared according to the general process illustrated and described in U.S. Pat. No. 4,800,198 issued Jan. 24, 1989 entitled "Method of Inducing the Differentiation of Malignant Cells With Secosterol", the description of which is specifically incorporated herein by reference.

The above secosterol compounds are employed in cosmetic compositions, formulations thereof and methods of using for the treatment of such skin conditions as dry skin (lack of dermal hydration), undue skin slackness (i.e., insufficient skin firmness) and insufficient sebum secretion. The cosmetic compositions are also effective in the general preservation, conditioning and protecting of the skin, e.g., against wrinkles.

Cosmetic compositions for use in the above-mentioned treatment of skin comprise a cosmetically effective amount of one or more secosterol compound as the active ingredient and a suitable carrier. A cosmetically effective amount of such compounds for use in accordance with this invention is from about 0.001 μg to about 10.0 μg per gm of composition. A concentration of 0.01 μg per gm of the composition is preferred.

The cosmetic compositions of this invention are formulated preferably as creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers and antioxidants may also be included as well as agents imparting color or fragrance if desired.

Cosmetic creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Cosmetic ointments may be formulated by mixing a solution of the active ingredient in a vegetable oil such as almond oil with warm soft paraffin and allowing the mixture to cool. A typical example of such an ointment is one which includes about 30% almond oil, and about 70% white soft paraffin by weight.

Cosmetic lotions may be conveniently prepared by dissolving the active ingredient, in a suitable high molecular weight alcohol such as propylene glycol or polyethylene glycol.

One or more additional substances which have therapeutic effects on the skin may also be incorporated in the cosmetic compositions. Thus in one embodiment of this invention the composition also contains one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are β-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include other compounds known to have a beneficial effect on skin. Such compounds include retinoids such as Vitamin A, in an amount of about 0.003%–0.3% by weight and chromanols such as Vitamin E or a derivative thereof in an amount of about 0.1–10% by weight, both based on the weight of the composition. Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition.

Topical application and intraperitoneal injection of cosmetic compositions of this invention was found to be cosmetically effective in field studies. In a typical example, topical application of a lotion containing 0.01 μg of a secosterol compound per gram of lotion to the skin of nude mice for five weeks resulted in improved skin condition.

The cosmetic efficacy of compositions containing secosterol compounds in accordance with this invention was determined by the following procedures:

Two treatment groups of six mice each were available with Group I being controls, and Group II being the treatment group with Homo-pregna calciferol. Three mice in each group received either the control vehicle only or the Homo-pregna calciferol treatment topically (t) and three mice in each group received either the control vehicle only or the Homo-pregna calciferol treatment intraperitoneally (ip) three times a week for 5 weeks.

Replicas were made about 48 hours after the last treatment of the backs of 5 control animals and 4 experimental animals. Silflo TM silicone rubber was spread onto the rear half of each mouse back (anesthetized with diethyl ether) and allowed to polymerize for 5 to 7 minutes. These silicone rubber "negative" replicas were stored in glassine envelopes until polyethylene "positive" replicas were made. The procedures for prepring both the negative and positive replicas will hereinafter be described.

The nine positive replicas were coated with 60 nm gold and examined in a JEOL JSM-35C scanning electron microscope at 15 kV accelerating voltage. Differences between replicas were evident to the unaided eye and from Polaroid micrographs made of each replica at X12 to form a montage of the entire surface. Micrographs were also made at X100 and X200 to differentiate fine details of skin surface condition.

Figure 2:
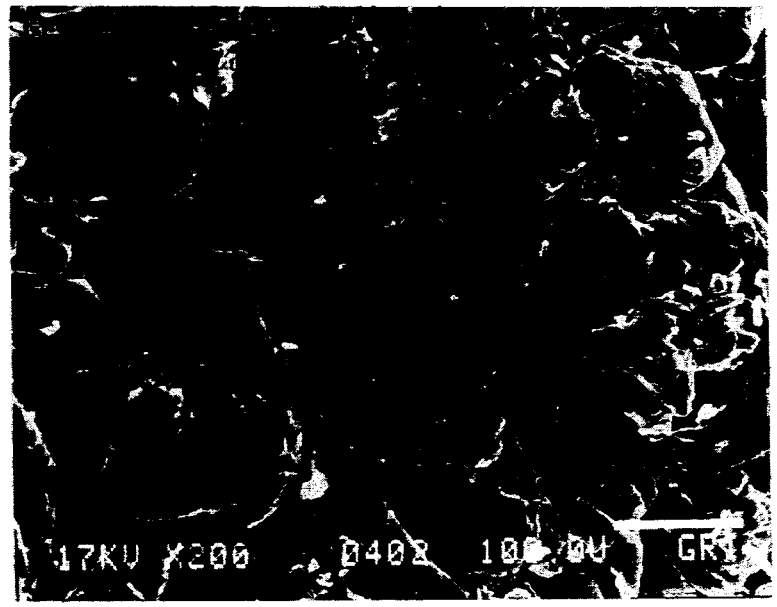
FIG. 2 is a photomicrograph at ×200 magnification of a skin replica of a second control mouse treated intraperitoneally with a propylene glygol control vehicle.
Figure 3:
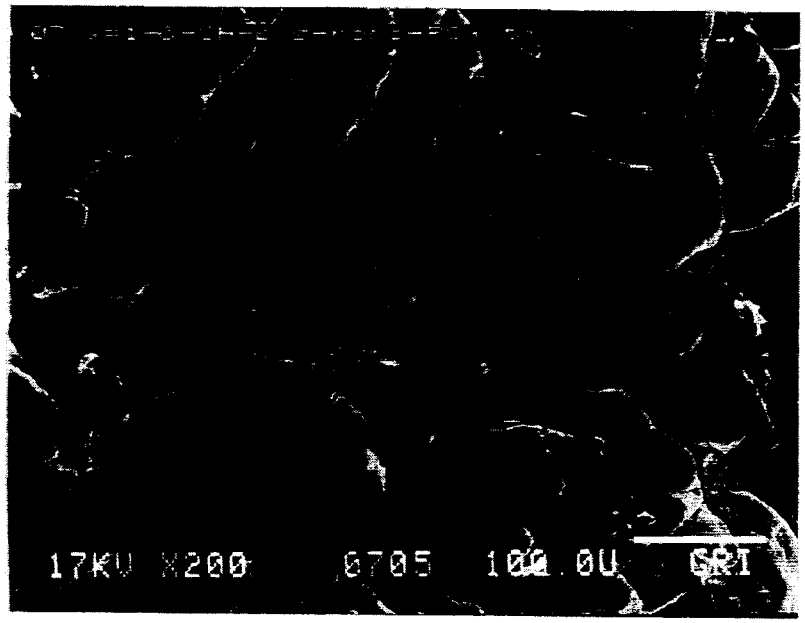
FIG. 3 is a photomicrograph at ×200 magnification of a skin replica of an experimental mouse treated topically with 1α-hydroxy-bis-homopregnacalciferol.
Figure 4:
FIG. 4 is a photomicrograph at ×200 magnification of a skin replica of a second experimental mouse treated topically with 1α-hydroxy-bis-homo-pregnacalciferol.
Figure 5:
FIG. 5 is a photomicrograph at ×200 magnification of a skin replica of an experimental mouse treated intraperitoneally with 1α-hydroxy-bis-homo-pregnacalciferol.
Figure 6:
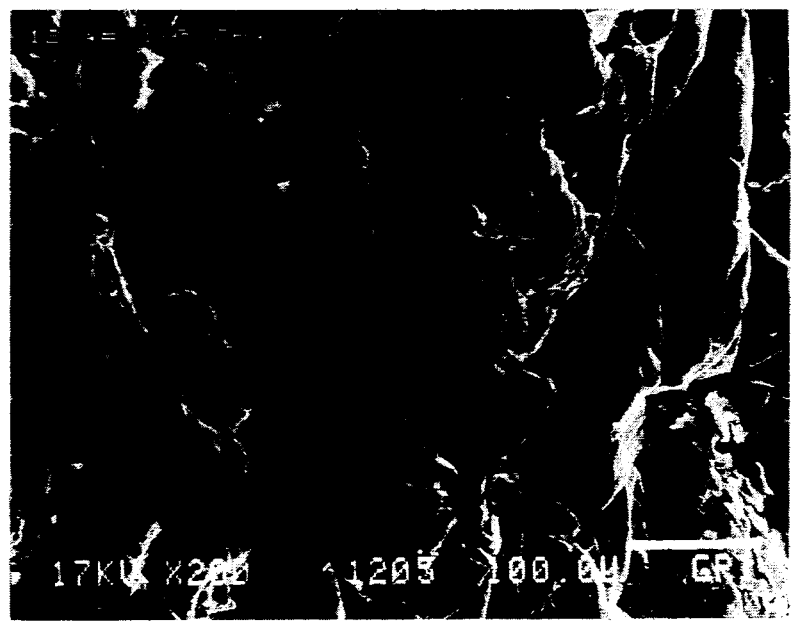
FIG. 6 is a photomicrograph at ×200 magnification of a skin replica of a second experimental mouse treated intraperitoneally with 1α-hydroxy-bis-homo-pregnacalciferol.

FIGS. 1 and 2 illustrate the skin surface condition of two of the control mice treated topically and intraperitonally with a propylene glycol vehicle only. FIGS. 3 and 4 illustrate the skin condition of two of the experimental mice treated topically with 1α-hydroxy-bis-homo-pregnacalciferol (homo-pregna) whereas FIGS. 5 and 6 illustrate the skin condition of two of the experimental mice treated intraperitoneally with 1α-hydroxy-bis-homopregnacalciferol.

The results of the above experiments were that the low magnification (×12) montages of the nine skin replicas could be ranked into three groups according to visible wrinkling and overall skin surface roughness. The best skin condition (rank 1) was exhibited by sample #8 which was treated with Homo-pregna. The next best were #5, #6 and #7 which were all Homo-pregna treatments, but which could not be distinguished at this low magnification with #1 and #3 which were controls. Two controls could be placed alone in a third rank having the roughest skin (Table 1).

Details of the skin surface such as stratum corneum desquamation, scaling, size and plumpness of skin divisions, were visible on higher magnification (X100 and X200) micrographs and used to rank the replicas from 1=best skin to 6=worst skin (Tables 1 and 2). The treated samples ranked 1 to 4, and the five controls ranked 5 and 6. The top-ranked four included all of the Homo-pregna samples (#5, #, #7 and #8). There was no discernible difference between topical and intraperitoneal Homo-pregna treated samples, i.e. #5, #6, #7 and #8.

As a result of these experiments, it may be concluded that topical and intraperitoneal treatments of nude mice with secosterol compounds produce visible changes in skin surface condition as seen on replicas. Treated samples showed less gross wrinkling and scaling and more smooth, plump, rounded skin microtopography than the respective controls. Topical treatment could not be differentiated from intraperitoneal treatment.

TABLE 1

SEM OF MOUSE SKIN REPLICAS

| No. | Treatment | Rank*(×12) | Rank*(×100,200) |
|---|---|---|---|
| #1 | c-t control | 2 | 6 |
| #2 | c-t control | 3 | 6 |
| #3 | c-t control | 3 | 6 |
| #4 | c-ip control | 2 | 6 |
| #5 | a-t Homo-pregna | 2 | 2 |
| #6 | a-t Homo-pregna | 2 | 4 |
| #7 | a-ip Homo-pregna | 2 | 3 |
| #8 | a-ip Homo-pregna | 1 | 1 |
| #9 | c-ip control | 2 | 5 |

Treatments:
a = Homo-pregnacalciferol
c = Control, vehicle only
t = topical, 80 ng Homo-pregnacalciferol/20 μl propylene glycol applied 3 times per week
ip = intraperitoneal, 25 ng Homo-pregnacalciferol/50 μl propylene glycol given 3 times per week

TABLE 2

RANKING OF MOUSE SKIN REPLICAS

| Rank* | Treatment | Rank@(×12) |
|---|---|---|
| 1 | #8 a-ip | 1 |
| 2 | #5 a-t | 2 |
| 3 | #7 a-ip | 2 |
| 4 | #6 a-t | 2 |
| 5 | #9 c-ip | 3 |
| 6 | #1 c-t | 2 |
| 6 | #2 c-t | 3 |
| 6 | #3 c-t | 2 |
| 6 | #4 c-ip | 2 |

*Scanning electron micrographs at ×100 and ×200 were judged for skin condition and ranked, with 1 = best (smoothest, plumpest, least scaling) and 6 = worst (roughest, most scaling).
@Photo montages at ×12 magnification were made of each 25 mm diameter replica and ranked for skin condition, with 1 = best (smoothest) and 3 = worst (roughest, more wrinkled).
Treatments:
a = Homo-pregnacalciferol
c = Control, vehicle only
t = topical
ip = intraperitoneal The skin replication techniques utilized in preparing the "negative" and "positive" replicas in order to perform the above described experiments and the photomicrographs of FIGS. 1-6 will now be described.

A. SILFLO NEGATIVE REPLICAS

1. Mix Silflo well before dispensing. Put Silflo into plastic syringe, 5 or 10 ml size.

2. Measure out 0.4 to 0.8 ml onto glassine paper or small weighing dish. The amount depends on the area to be replicated and the rate of polymerization desired.

3. Add 1 drop thinner per 0.4 ml Silflo. (Steps 1–3 can be done in advance.)

4. Place TCOM adhesive ring on skin site(s) to be replicated. (This ring was omitted on the mice.)

5. Add 1 drop catalyst per 0.4 ml Silflo and start timer. These amounts can be adjusted if replica sets too fast or too slowly. Silflo should not stiffen until ~2 min. after catalyst addition and should set tack-free 3~3.5 min. after catalyst.

6. Mix thoroughly with spatula tip for 20–25 sec.

6a. To remove air bubbles, place Silflo dish into small vacuum desiccator and evacuate with mechanical pump until silicone rubber foams up once and collapses; remove at once from vacuum and apply to skin. (Elapsed time should be ~1 min. since addition of catalyst.)

7. Spread Silflo mixture quickly onto skin site with spatula.

8. Let Silflo set for a minimum of 5 minutes, without any movement of the subject. Check that the replica has polymerized before proceeding.

9. Peel off the replica and place it in a dust and lint-free container.

B. POLYETHYLENE POSITIVE REPLICAS

1. Allow Silflo replicas to polymerize completely at room temperature, usually overnight, but 6 hours is sufficient.

2. Place replicas in a dish such as glass petri dish, aluminum weighing dish or on a metal tray. Place a shallow brass ring (or other retaining device which serves as a mold for the polyethylene) on the replica. The diameter of the ring mold will depend on the diameter of the SEM specimen carrier being used (usually 15mm or 25mm).

3. Place replicas into 160°~170° C. oven for a short time, ~5 min. This heating of the replicas drives off moisture and other volatiles.

4. Remove replicas from oven. Fill each brass ring mold with polyethylene pellets.

5. Replace replicas in oven and heat until polyethylene has melted completely and covers the replica surface ( ~15 min.).

6. Turn oven off, open oven door and allow replicas to cool slowly. Too rapid cooling can cause cracks and artifacts in the polyethylene.

7. When replicas have cooled almost to room temperature, they can be removed from the oven. Peel off the Silflo replica from the polyethylene replica, which remains within its metal ring.

8. The hardened polyethylene replica can be sputter-coated with gold and examined in the SEM without removing it from its brass ring mold. The replica can also be pushed out of the ring mold and replaced in it again, if necessary.

The visible changes in skin surface condition (as shown in FIGS. 3-6 versus FIGS. 1-2), is in marked contrast with that of compositions containing ergocalciferol or cholecalciferol. Topical application of compositions containing ergocalciferol, for instance, were of low cosmetic efficacy and in fact resulted in decreased skin elasticity (See Table I in Dikstein et al Reissue No. 33,107). Moreover, since it is known that ergocalciferol and cholecalciferol are absorbed into the bloodstream through the skin, it is likely that doses of such compounds applied to large areas of the skin or applied chronically, even in the minimal active dose, cause systemic effects. Further, since the compounds of the present invention have little or no classical vitamin D activities, no side effects were expected or observed.

We claim:

1. A method of treating cosmetic skin conditions consisting of lack of adequate skin firmness, wrinkles, lack of dermal hydration and insufficient sebum secretion which comprises topically applying to the skin a cosmetic composition having a compound of the formula:

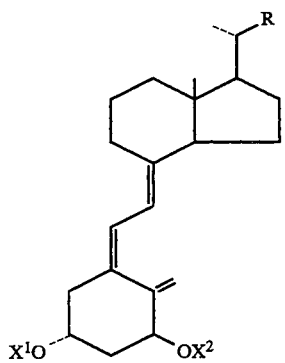

where R is hydrogen, methyl, ethyl or propyl and where each of $X^1$ and $X^2$ represent, independently, hydrogen, an acyl group, or a hydroxy-protecting group, said compound present in the composition in an amount from about 0.001 μg/gm to about 10.0 μg/gm of the composition.

2. The method of claim 1 wherein R is hydrogen.
3. The method of claim 1 wherein R is methyl.
4. The method of claim 1 wherein R is ethyl.
5. The method of claim 1 wherein R is propyl.

* * * * *

UNITED STATES PATENT AND TRADEMARK OFFICE
CERTIFICATE OF CORRECTION

PATENT NO. : 5,366,731
DATED : November 22, 1994
INVENTOR(S) : Hector F. DeLuca et al It is certified that error appears in the above-indentified patent and that said Letters Patent is hereby corrected as shown below:

Column 1, line 7, insert the following paragraph as the first paragraph of the specification:
--This invention was made with United States Government support awarded by the National Institutes of Health (NIH), Grant No. DK14881. The United States Government has certain rights in this invention.--

Signed and Sealed this

Sixteenth Day of May, 1995

Attest:

BRUCE LEHMAN

*Attesting Officer*  *Commissioner of Patents and Trademarks*